US012599343B2

(12) United States Patent
Kim et al.

(10) Patent No.: US 12,599,343 B2
(45) Date of Patent: Apr. 14, 2026

(54) MEASURING APPARATUS TO MEASURE PET'S HEALTH STATUS AND OPERATING METHOD THEREOF

(71) Applicant: FRANKLIN TECHNOLOGY INC., Seoul (KR)

(72) Inventors: Ok Chae Kim, Seoul (KR); Changsoo Yu, Hwaseong-si (KR)

(73) Assignee: FRANKLIN TECHNOLOGY INC., Seoul (KR)

( * ) Notice: Subject to any disclaimer, the term of this patent is extended or adjusted under 35 U.S.C. 154(b) by 23 days.

(21) Appl. No.: 18/786,592

(22) Filed: Jul. 29, 2024

(65) Prior Publication Data

US 2025/0152111 A1 May 15, 2025

(30) Foreign Application Priority Data

Nov. 15, 2023 (KR) ........................ 10-2023-0158226

(51) Int. Cl.
| | |
|---|---|
| *A61B 5/00* | (2006.01) |
| *A61B 5/0205* | (2006.01) |
| *A61B 5/05* | (2021.01) |
| *A61B 5/11* | (2006.01) |
| *H04L 9/08* | (2006.01) |
| *H04L 9/40* | (2022.01) |

(52) U.S. Cl.
CPC .......... *A61B 5/7465* (2013.01); *A61B 5/0064* (2013.01); *A61B 5/0205* (2013.01); *A61B 5/05* (2013.01); *A61B 5/1113* (2013.01); *A61B*

5/7246 (2013.01); *H04L 9/0894* (2013.01); *H04L 63/0428* (2013.01); *A61B 2503/40* (2013.01)

(58) Field of Classification Search
CPC ... A61B 5/7465; A61B 5/0064; A61B 5/0205; A61B 5/05; A61B 5/1113; A61B 5/7246; A61B 2503/40; A61B 5/024; A61B 5/0507; A61B 5/0816; H04L 9/0894; H04L 63/0428; A01K 29/005; A01K 29/007

See application file for complete search history.

(56) References Cited

U.S. PATENT DOCUMENTS

| | | | | |
|---|---|---|---|---|
| 2005/0066910 A1* | 3/2005 | Tecott | .................... | A01K 1/031 |
| | | | | 119/421 |
| 2012/0180731 A1* | 7/2012 | Garner | .................. | A01K 1/031 |
| | | | | 119/417 |

(Continued)

FOREIGN PATENT DOCUMENTS

| | | |
|---|---|---|
| KR | 10-2015-0115028 A | 10/2015 |
| KR | 10-2085289 B1 | 4/2020 |

(Continued)

*Primary Examiner* — Ryan W Sherwin

(74) *Attorney, Agent, or Firm* — Park, Kim & Suh, LLC

(57) ABSTRACT

According to the present disclosure, a measuring apparatus and an operating method thereof are presented which measure a heart rate and a breathing rate of a pet by using a radar sensor, and then confirm whether a health status of the pet is abnormal based on the measured data, and when it is confirmed that the health status of the pet is abnormal, transmit a notification message to an electronic terminal of a pet owner to support the pet owner to more rapidly respond to health abnormality of the pet.

7 Claims, 2 Drawing Sheets

(56)          References Cited

U.S. PATENT DOCUMENTS

| | | | | | |
|---|---|---|---|---|---|
| 2014/0182519 | A1 * | 7/2014 | Tupin, Jr. | .............. | A61B 5/6822 |
| | | | | | 119/859 |
| 2020/0359605 | A1 * | 11/2020 | Maher | .................. | A01K 27/009 |
| 2023/0143669 | A1 * | 5/2023 | O'Dwyer | .............. | A01K 15/02 |
| | | | | | 340/573.3 |

FOREIGN PATENT DOCUMENTS

| | | | | | |
|---|---|---|---|---|---|
| KR | 102139048 | B1 * | 7/2020 | ........... | A61B 5/6887 |
| KR | 10-2022-0082664 | A | 6/2022 | | |
| KR | 10-2451323 | B1 | 10/2022 | | |
| KR | 10-2022-0158497 | A | 12/2022 | | |
| KR | 10-2023-0046797 | A | 4/2023 | | |
| KR | 20230073524 | A * | 5/2023 | ........... | A01K 29/005 |

* cited by examiner

Fig. 2

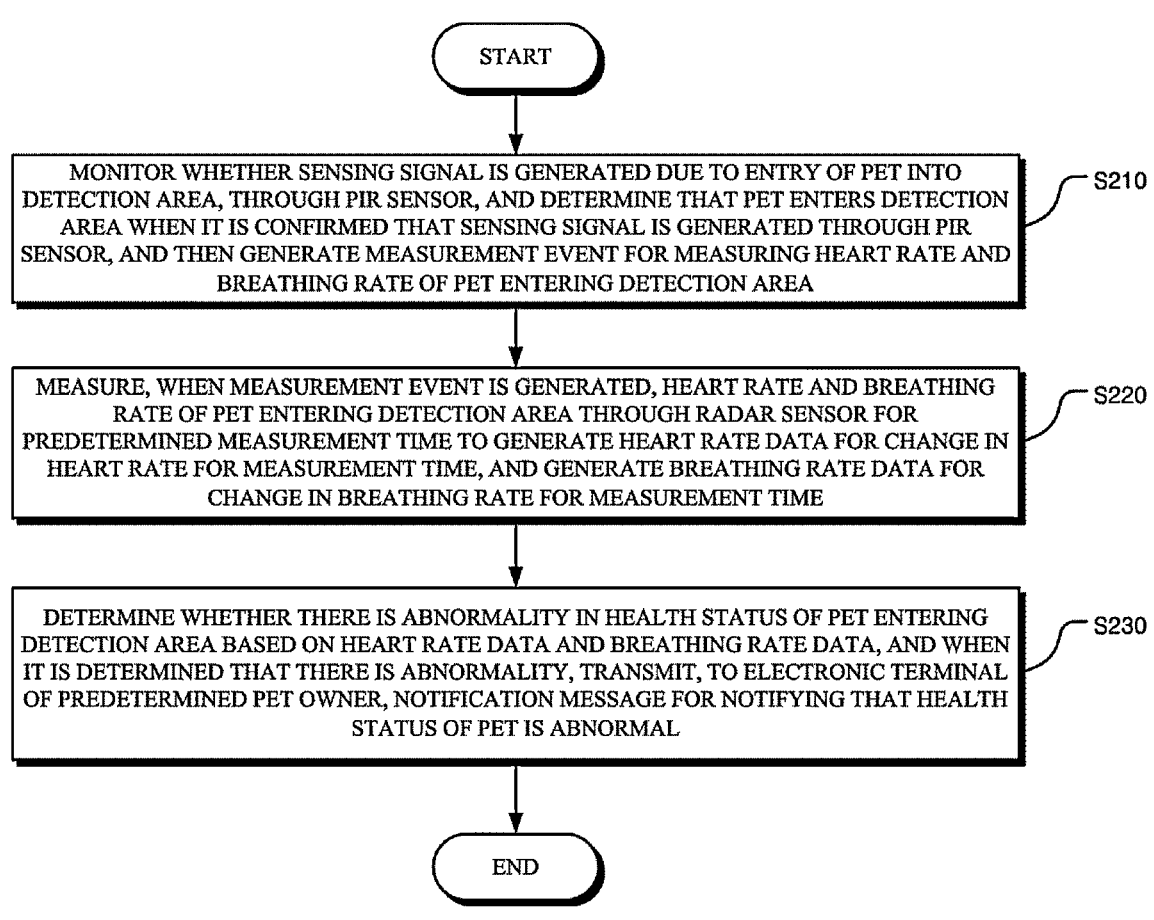

START

MONITOR WHETHER SENSING SIGNAL IS GENERATED DUE TO ENTRY OF PET INTO DETECTION AREA, THROUGH PIR SENSOR, AND DETERMINE THAT PET ENTERS DETECTION AREA WHEN IT IS CONFIRMED THAT SENSING SIGNAL IS GENERATED THROUGH PIR SENSOR, AND THEN GENERATE MEASUREMENT EVENT FOR MEASURING HEART RATE AND BREATHING RATE OF PET ENTERING DETECTION AREA — S210

MEASURE, WHEN MEASUREMENT EVENT IS GENERATED, HEART RATE AND BREATHING RATE OF PET ENTERING DETECTION AREA THROUGH RADAR SENSOR FOR PREDETERMINED MEASUREMENT TIME TO GENERATE HEART RATE DATA FOR CHANGE IN HEART RATE FOR MEASUREMENT TIME, AND GENERATE BREATHING RATE DATA FOR CHANGE IN BREATHING RATE FOR MEASUREMENT TIME — S220

DETERMINE WHETHER THERE IS ABNORMALITY IN HEALTH STATUS OF PET ENTERING DETECTION AREA BASED ON HEART RATE DATA AND BREATHING RATE DATA, AND WHEN IT IS DETERMINED THAT THERE IS ABNORMALITY, TRANSMIT, TO ELECTRONIC TERMINAL OF PREDETERMINED PET OWNER, NOTIFICATION MESSAGE FOR NOTIFYING THAT HEALTH STATUS OF PET IS ABNORMAL — S230

END

MEASURING APPARATUS TO MEASURE PET'S HEALTH STATUS AND OPERATING METHOD THEREOF

CROSS-REFERENCE TO RELATED APPLICATIONS

This application claims priority to and the benefit of Korean Patent Application No. 10-2023-0158226 filed in the Korean Intellectual Property Office on Nov. 15, 2023, the entire contents of which are incorporated herein by reference.

TECHNICAL FIELD

The present disclosure relates to a measuring apparatus installed in a predetermined detection area indoors and measuring a pet's health status, and an operating method thereof.

BACKGROUND ART

Recently, as the number of people raising pets increases, there is an increased demand for technology that supports constant monitoring of the pet's health status and enables immediate action when an abnormality occurs in the pet's health.

In this regard, radar sensors have recently emerged that can measure a pet's heart rate or breathing rate by radiating radar to the pet.

When such a radar sensor can be used, data on pet's heart rate and breathing rate can be secured, so introduction of technology can be considered, which determines whether there is an abnormality in the pet's health status by analyzing the data secured as such.

Specifically, introduction of technology can be considered, in which after establishing a predetermined detection area indoors, it is monitored whether a pet enters the detection area, and when it is determined that the pet enters the detection area, data on the heart rate and the breathing rate of the pet is obtained through the radar sensor, and then the obtained data is analyzed to determine whether the health status of the pet is abnormal.

If technology to measure the health status of the pet is introduced, it will be possible to raise the pets in a more stable environment in that when pet owners who raise the pets confirm that the health statuses of the pets are abnormal, the pet owners can immediately visit a veterinary hospital and receive appropriate medical treatment for their pets.

SUMMARY OF THE INVENTION

The present disclosure has been made in an effort to present a measuring apparatus and an operating method thereof which measure a heart rate and a breathing rate of a pet by using a radar sensor, and then confirm whether a health status of the pet is abnormal based on the measured data, and when it is confirmed that the health status of the pet is abnormal, transmit a notification message to an electronic terminal of a pet owner to support the pet owner to more rapidly respond to health abnormality of the pet.

An exemplary embodiment of the present disclosure provides a measuring apparatus installed in a predetermined detection area indoors, and measuring a health status of a pet, which includes: a passive infrared (PIR) sensor for detecting a pet entering the detection area; a radar sensor for measuring a heart rate and a breathing rate of the pet entering the detection area; a measurement event generator monitoring whether a sensing signal is generated due to the entry of the pet into the detection area, through the PIR sensor, and determining that the pet enters the detection area when it is confirmed that the sensing signal is generated through the PIR sensor, and then generating a measurement event for measuring the heart rate and the breathing rate of the pet entering the detection area; a data generator measuring, when the measurement event is generated, the heart rate and the breathing rate of the pet entering the detection area through the radar sensor for a predetermined measurement time to generate heart rate data for a change in heart rate for the measurement time, and generate breathing rate data for the change in breathing rate for the measurement time; and a notification transmitter determining whether there is an abnormality in the health status of the pet entering the detection area based on the heart rate data and the breathing rate data, and when it is determined that there is the abnormality, transmitting, to an electronic terminal of a predetermined pet owner, a notification message for notifying that the health status of the pet is abnormal.

Further, another exemplary embodiment of the present disclosure provides an operating method of a measuring apparatus installed in a predetermined detection area indoors, and measuring a health status of a pet, which includes: monitoring whether a sensing signal is generated due to the entry of the pet into the detection area, through the PIR sensor, and determining that the pet enters the detection area when it is confirmed that the sensing signal is generated through the PIR sensor, and then generating a measurement event for measuring the heart rate and the breathing rate of the pet entering the detection area; measuring, when the measurement event is generated, the heart rate and the breathing rate of the pet entering the detection area through the radar sensor for a predetermined measurement time to generate heart rate data for a change in heart rate for the measurement time, and generate breathing rate data for the change in breathing rate for the measurement time; and determining whether there is an abnormality in the health status of the pet entering the detection area based on the heart rate data and the breathing rate data, and when it is determined that there is the abnormality, transmitting, to an electronic terminal of a predetermined pet owner, a notification message for notifying that the health status of the pet is abnormal.

According to an exemplary embodiment of the present disclosure, a measuring apparatus and an operating method thereof are presented which measure a heart rate and a breathing rate of a pet by using a radar sensor, and then confirm whether a health status of the pet is abnormal based on the measured data, and when it is confirmed that the health status of the pet is abnormal, transmit a notification message to an electronic terminal of a pet owner to support the pet owner to more rapidly respond to health abnormality of the pet.

BRIEF DESCRIPTION OF THE DRAWINGS

FIG. 2 is a flowchart illustrating an operating method of a measuring apparatus according to an exemplary embodiment of the present disclosure.

DETAILED DESCRIPTION

Figure 1:
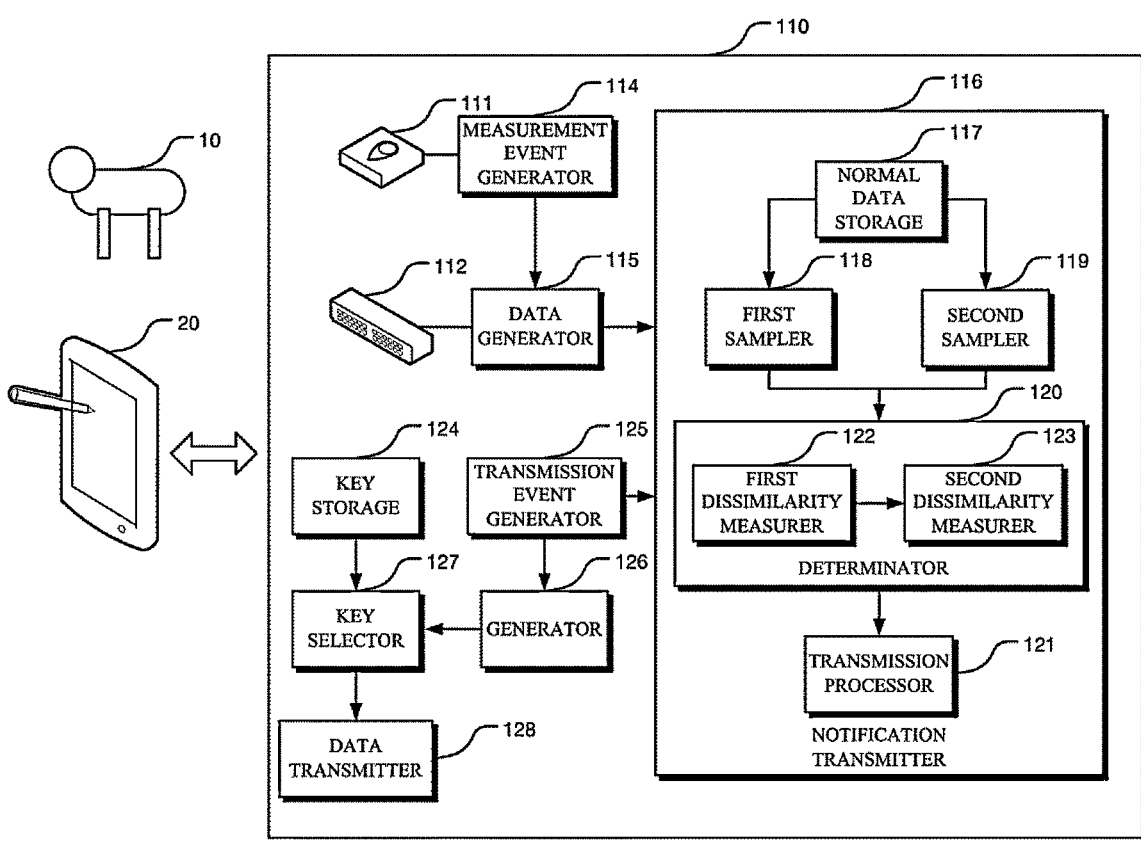
FIG. 1 is a diagram illustrating a structure of a measuring apparatus according to an exemplary embodiment of the present disclosure.

Hereinafter, exemplary embodiments of the present disclosure will be described in detail with reference to the accompanying drawings. The description does not limit the present disclosure to specific exemplary embodiments, and it should be understood that the present disclosure covers all the modifications, equivalents and replacements included within the idea and technical scope of the present disclosure. In describing each drawing, like reference numerals refer to like elements and if not contrarily defined, all terms used herein including technological or scientific terms have the same meanings as those generally understood by a person with ordinary skill in the art.

In this document, unless explicitly described to the contrary, the word "comprise" and variations such as "comprises" or "comprising", will be understood to imply the inclusion of stated elements but not the exclusion of any other elements. Further, in various exemplary embodiments of the present disclosure, each of the components, functional blocks or means may be constituted by one or more lower components and electrical, electronic, and mechanical functions performed by respective components may be implemented as various known devices or mechanical elements including an electronic circuit, an integrated circuit, an Application Specific Integrated Circuit (ASIC), etc., and the respective components may be separately implemented or two or more components may be integrated into one and implemented.

Meanwhile, blocks of the accompanying block diagram or steps of a flowchart may be appreciated as meaning compute program instructions mounted on a processor or a memory of data processible equipment such as a universal computer, a special computer, a portable notebook computer, a network computer, etc., and performing designated functions. Since the computer program instructions may be stored in a memory provided in a computer device or a computer readable memory, functions described in blocks of a block diagram or steps of a flowchart may be produced as a manufactured object including an instruction mean performing the functions. Moreover, each block or each step may represent a part of a module, a segment, or a code that includes one or more executable instructions for executing a specified logical function(s). It should also be noted that in some replaceable embodiments, the functions mentioned in the blocks or steps may also be executed differently from a predetermined order. For example, two blocks or steps that are subsequently illustrated are substantially simultaneously carried out, or may be performed in a reverse order, and in some cases, the functions may be performed while some blocks or steps are omitted.

FIG. 1 is a diagram illustrating a structure of a measuring apparatus according to an exemplary embodiment of the present disclosure.

The measurement apparatus 110 according to the present disclosure as an apparatus installed in a predetermined detection area indoors and measuring a health status of a pet includes a passive infrared (PIR) sensor 111, a radar sensor 112, a measurement event generator 114, a data generator 115, and a notification transmitter 116.

The PIR sensor 111 as a sensor for detecting a pet entering the detection area through sensing of infrared rays radiated from the pet entering the detection area is configured to generate a sensing signal when it is determined that the pet enters the detection area.

The radar sensor 112 as a frequency modulated continuous wave (FMCW) scheme multi-channel support sensor for measuring a heart rate and a breathing rate of the pet entering the detection area by using a radar may measure a predetermined heart rate per unit time (e.g., heart rate per minute), and a predetermined breathing rate per unit time (e.g., breathing rate per minute).

In such a situation, the measurement event generator 114 may monitor whether a detection signal is generated due to the entry of the pet into the detection area through the PIR sensor 111.

At this time, when it is confirmed that the detection signal is generated through the PIR sensor 111 due to the entry of a predetermined pet 10 into the detection area, the measurement event generator 114 determines that the pet 10 enters the detection area, and then generates a measurement event for measuring the heart rate and the breathing rate of the pet 10 entering the detection area.

When the measurement event occurs, the data generator 115 measures the heart rate and the breathing rate of the pet 10 entering the detection area through the radar sensor 112 for a predetermined measurement time to generate heart rate data for a change in heart rate for the measurement time, and generate breathing rate data for the change in breathing rate for the measurement time.

For example, in a case where the measurement time is '30 minutes', when the measurement event occurs, the data generator 115 measures the heart rate and the breathing rate of the pet 10 entering the detection area through the radar sensor 112 to generate heart rate data for a change in heart rate for '30 minutes', and generate breathing rate data for a change in breathing rate for '30 minutes'.

The notification transmitter 116 determines whether there is an abnormality in the health status of the pet 10 entering the detection area based on the heart rate data and the breathing rate data, and when it is determined that there is the abnormality, the notification transmitter 116 transmits, to an electronic terminal 20 of a predetermined pet owner, a notification message for notifying that the health status of the pet 10 is abnormal.

In this case, according to an exemplary embodiment of the present disclosure, the notification transmitter 116 may include a normal data storage 117 a first sampler 118, a second sampler 119, a determinator 120, and a transmission processor 121.

The normal data storage 117 stores predetermined normal heart rate data and predetermined normal breathing rate data.

Here, the normal heart rate data means data for a change in heart rate obtained from a pet in a normal health status for a time which is the same as the measurement time, and the normal breathing rate data means data for a change in breathing rate obtained from the pet in the normal health status for the time which is the same as the measurement time. For example, in the case where the measurement time is '30 minutes', the normal heart rate data means data for a change in heart rate pre-obtained from the pet in the normal health status for '30 minutes', and the normal breathing rate data means data for a change in breathing rate pre-obtained from the pet in the normal health status for '30 minutes'.

When the heart rate data and the breathing rate data are generated through the data generator 115, the first sampler 118 samples the heart rate to obtain a plurality of sample heart rates from the heart rate data at a predetermined sampling period interval, and samples the breathing rate from the breathing rate data at the sampling period interval to obtain a plurality of sample breathing rates.

For example, in a case where the sampling period is '3 minutes', the first sampler 118 samples the heart rate at an interval of '3 minutes' from the heart rate data which is the data for the change in heat rate for '30 minutes' to obtain 10 sample heart rates, and samples the breathing rate at an interval of '3 minutes' from the breathing rate data which is the data for the change in breathing rate for '30 minutes' to obtain 10 sample breathing rates.

The second sampler 119 samples the heart rate from the normal heart rate data at the sampling period interval to obtain a plurality of normal sample heart rates, and samples the breathing rate from the normal breathing rate data at the sampling period interval to obtain a plurality of normal sample breathing rates.

In this regard, as in the above-described example, in the case where the sampling period is '3 minutes', the second sampler 119 samples the heart rate from the normal heart rate data which is the data for the change in normal heat rate for '30 minutes' at an interval of '3 minutes' to obtain 10 normal sample heart rates, and samples the breathing rate from the normal breathing rate data which is the data for the change in normal breathing rate for '30 minutes' at the interval of '3 minutes' to obtain 10 normal sample breathing rates.

The determinator 120 measures a first dissimilarity between the plurality of sample heart rates and the plurality of normal sample heat rates, and a second dissimilarity between the plurality of sample breathing rates and the plurality of normal sample breathing rates, and then determines whether the health status of the pet 10 entering the detection area is abnormal based on the first dissimilarity and the second dissimilarity.

In this case, according to an exemplary embodiment of the present disclosure, the determinator 120 may include a first dissimilarity measurer 122 and a second dissimilarity measurer 123.

The first dissimilarity measurer 122 performs L1 normalization of scaling a size so that a total sum becomes 1 with respect to the plurality of sample heart rates, and then generate a first probability distribution having normalized values as a probability, and performs the L1 normalization of scaling the size so that the total sum becomes 1 with respect to the plurality of normal sample heart rates, and then generates a second probability distribution having normalized values as the probability, and then measures a Kullback-Leibler Divergence between the first probability distribution and the second probability distribution as the first dissimilarity between the plurality of sample heart rates and the plurality of normal sample heart rates.

In this regard, as in the above-described example, in a case where 10 sample heart rates and 10 normal sample heart rates are sampled, the first dissimilarity measurer 122 may perform the L1 normalization of scaling a size so that the total sum becomes 1 with respect to the 10 sample heart rates, and perform the L1 normalization of scaling the size so that the total sum becomes 1 even with respect to the 10 normal sample heart rates. Here, the L1 normalization means a normalization scheme which allows a sum of data to become 1, and at the same time, allows a size to be scaled to a value between 0 and 1. The normalization may be performed by dividing a value of each data by a total sum of the data.

In this way, the values for which L1 normalization is performed have values between 0 and 1 with a total sum of 1, so the values may be regarded as the probability for each data that makes up the probability distribution. As a result, the first dissimilarity measurer 122 may generate a first probability distribution having the normalization value for the 10 sample heart rates as the probability, and generate a second probability distribution having the normalization value for the 10 normal sample heart rates as the probability.

Then, the first dissimilarity measurer 122 may measure the Kullback-Leibler Divergence between the first probability distribution and the second probability distribution as the first dissimilarity between the 10 sample heart rates and the 10 normal sample heart rates. Here, the Kullback-Leibler Divergence is an indicator indicating a difference between both probability distributions, and if there are probability distributions P and Q, the Kullback-Leibler Divergence between both probability distributions may be calculated as $$\sum_i P(i) \log \frac{P(i)}{Q(i)},$$

and the larger the value, the less similar the both probability distributions are.

The second dissimilarity measurer 123 performs L1 normalization of scaling a size so that a total sum becomes 1 with respect to the plurality of sample breathing rates, and then generate a third probability distribution having normalized values as a probability, and performs the L1 normalization of scaling the size so that the total sum becomes 1 with respect to the plurality of normal sample breathing rates, and then generates a fourth probability distribution having normalized values as the probability, and then measures a Kullback-Leibler Divergence between the third probability distribution and the fourth probability distribution as the second dissimilarity between the plurality of sample breathing rates and the plurality of normal sample breathing rates.

In this regard, as in the above-described example, in a case where 10 sample breathing rates and 10 normal sample breathing rates are sampled, the second dissimilarity measurer 123 may perform the L1 normalization of scaling a size so that the total sum becomes 1 with respect to the 10 sample breathing rates, and perform the L1 normalization of scaling the size so that the total sum becomes 1 even with respect to the 10 normal sample breathing rates.

In this way, the values for which L1 normalization is performed have values between 0 and 1 with a total sum of 1, so the values may be regarded as the probability for each data that makes up the probability distribution. As a result, the second dissimilarity measurer 123 may generate a third probability distribution having the normalization value for the 10 sample breathing rates as the probability, and generate a fourth probability distribution having the normalization value for the 10 normal sample breathing rates as the probability.

Then, the second dissimilarity measurer 123 may measure the Kullback-Leibler Divergence between the third probability distribution and the fourth probability distribution as the second dissimilarity between the 10 sample breathing rates and the 10 normal sample breathing rates.

In this case, according to an exemplary embodiment of the present disclosure, when the first dissimilarity and the second dissimilarity are measured, the determinator 120 compares the first dissimilarity with a predetermined first threshold, and compare the second dissimilarity with a predetermined second threshold, and when the first dissimilarity is confirmed to exceed the first threshold, or the second dissimilarity is confirmed to exceed the second threshold, the determinator 120 may determine that the health status of the pet 10 entering the detection area is abnormal.

In other words, when a state in which the first dissimilarity exceeds the first threshold, that is, a state in which the plurality of sample heart rates and the plurality of normal sample heart rates are not similar to each other, or a state the second dissimilarity exceeds the second threshold, that is, a state in which the plurality of sample breathing rates and the plurality of normal sample breathing rates are not similar to each other is confirmed, the determinator 120 may determine that the health status of the pet 10 is abnormal in that it may be regarded that the heart rate or the breathing rate of the pet 10 is not normal.

Further, when it is confirmed that the first dissimilarity does not exceed the first threshold, and at the same time, it is confirmed that the second dissimilarity does not exceed the second threshold, the determinator 120 may determine that the health status of the pet 10 entering the detection area is abnormal only when it is confirmed that a value acquired by averaging an error between the first threshold and the first dissimilarity and an error between the second threshold and the second dissimilarity is equal to or less than a predetermined determination reference value.

In this regard, when both the first dissimilarity and the second dissimilarity do not exceed the first threshold and the second threshold, a situation similar to that when the heart rate and the breathing rate of the pet 10 are normal may be regarded, so it may be regarded that the health status of the pet 10 is unlikely to fall into the abnormality. Therefore, when both the first dissimilarity and the second dissimilarity do not exceed the first threshold and the second threshold, the determinator 120 may determine that the health status of the pet 10 is abnormal only when the value acquired by averaging the error between the first threshold and the first dissimilarity and the error between the second threshold and the second dissimilarity is equal to or less than the determination reference value, that is, when a dissimilarity level considering both dissimilarities is large to approach a predetermined reference value.

When it is determined that the health status of the pet 10 entering the detection area is abnormal according to a determination result by the determinator 120, the transmission processor 121 may transmit the notification message for notifying that the health status of the pet 10 is abnormal to the electronic terminal 20 of the pet owner.

Through this, the per owner takes various measures for checking the health status of the pet 10 to early prevent a health of the pet 10 from being deteriorated.

According to an exemplary embodiment of the present disclosure, the measuring apparatus 110 may further include a key storage 124, a transmission event generator 125, a generator 126, a key selector 127, and a data transmitter 128.

The key storage 124 stores a first secret key and a second secret key for encrypting data, which are previously shared with the electronic terminal 20 of the pet owner. Here, each of the first secret key and the second secret key is assigned a different selection probability consisting of a percentage. For example, the first secret key and the second secret key may be assigned selection probabilities of '30(%)' and '70(%)', respectively. In addition, the first secret key and the second secret key are also stored in the electronic terminal 20 of the pet owner.

When receiving a providing request command of the heart rate data and the breathing rate data from the electronic terminal 20 of the pet owner after the notification message is transmitted to the electronic terminal 20 of the pet owner, the transmission event generator 125 generates a transmission event for encrypting the heart rate data and the breathing rate data, and transmitting the encrypted heart rate data and breathing rate data to the electronic terminal 20 of the pet owner.

The generator 126 checks a number corresponding to a day at a date of a current date and a number corresponding to a minute at a current time, and calculates a product between both numbers, and then performs a modulo operation using 101 as a divisor with respect to a calculated value to generate a result value constituted by integers between 0 and 100.

For example, when the current date when the transmission event is generated is 'Nov. 10, 2023' and the current time is '18:20:23', the generator 126 checks '10' which is a number corresponding to the day and '20' which is a number corresponding to the minute, and calculates a product between both numbers as '200', and then performs a modulo operation using 101 as a divisor with respect to the value to generate a result value of '20'.

The key selector 127 selects, as a reference probability, a selection probability having a smaller value among the selection probabilities assigned to the first secret key and the second secrete key, and then compares the result value and the reference probability, and selects any one secret key having the reference probability as the selection probability among the first secret key and the second secret key as a data encryption key when the result value is equal to or less than the reference probability, and selects the other one secret key not having the reference probability as the selection probability among the first secret key and the second secret key as the data encryption key when the result value is more than the reference probability.

In this regard, as in the above-described example, when a selection probability of '30(%)' is assigned to the first secret key and a selection probability of '70(%)' is assigned to the second secret key, and the result value is calculated as '20', the key selector 127 may select '30(%)' which is a selection probability of a smaller value among the selection probabilities assigned to the first secret key and the second secrete key as the reference probability, and then compare '20' which is the result value, and '30(%)' which is the reference probability. Then, since '20' which is the result value is equal to or less than '30(%)' which is the reference probability, the key selector 127 may select the first secret key which is a secret key having '30(%)' which is the reference probability as the selection probability among the first secret key and the second secret key as the data encryption key.

When selection of the data encryption key is completed, the data transmitter 128 encrypts each of the heart rate data and the breathing rate data based on the data encryption key, and transmits the encryption data to the electronic terminal 20 of the pet owner.

In this regard, as in the above-described example, when the first secret key is selected as the data encryption key, the data transmitter 128 may encrypt each of the heart rate data and the breathing rate data based on the first secret key, and transmit the encrypted data to the electronic terminal 20 of the pet owner.

At this time, according to an exemplary embodiment of the present disclosure, when the electronic terminal 20 of the pet owner receives the encrypted heart rate data and the encrypted breathing rate data from the measuring apparatus 110, the electronic terminal 20 of the pet owner checks the number corresponding to the day at the current date and the number corresponding to the minute at the current time, and calculates a product between both numbers, and then performs a modulo operation using 101 as a divisor with respect to the calculated value to generate the result value which is constituted by integers between 0 and 100.

In this regard, as in the above-described example, when the current date is 'Nov. 10, 2023' and the current time is '18:20:23', the electronic terminal 20 of the pet owner checks '10' which is a number corresponding to the day and '20' which is a number corresponding to the minute, and calculates a product between both numbers as '200', and then performs the modulo operation using 101 as the divisor with respect to the value to generate a result value of '20'.

In this way, when the generation of the result value is completed, the electronic terminal 20 of the pet owner may check the selection probabilities assigned to the first secret key and the second secret key stored in the electronic terminal 20 of the pet owner, and select the selection probability of the smaller value among the selection probabilities assigned to the first secret key and the second secret key as the reference probability, and then compares the result value and the reference probability, and selects any one secret key having the reference probability as the selection probability among the first secret key and the second secret key as a data decryption key when the result value is equal to or less than the reference probability, and select the other one secret key not having the reference probability as the selection probability among the first secret key and the second secret key as the data decryption key when the result value is more than the reference probability.

In this regard, as in the above-described example, when a selection probability of '30(%)' is assigned to the first secret key and a selection probability of '70(%)' is assigned to the second secret key, and the result value is calculated as '20', the electronic terminal 20 of the pet owner may select '30(%)' which is a selection probability of a smaller value among the selection probabilities assigned to the first secret key and the second secrete key as the reference probability, and then compare '20' which is the result value, and '30(%)' which is the reference probability. Then, since '20' which is the result value is equal to or less than '30(%)' which is the reference probability, the electronic terminal 20 of the pet owner may select the first secret key which is a secret key having '30(%)' which is the reference probability as the selection probability among the first secret key and the second secret key as the data decryption key.

As such, when the selection of the data decryption key is completed, the electronic terminal 20 of the pet owner may decrypt each of the encrypted heart rate data and the encrypted breathing rate data based on the data decryption key.

In this regard, as in the above-described example, when the first secret key is selected as the data decryption key, the electronic terminal 20 of the pet owner may decrypt each of the encrypted heart rate data and the encrypted breathing rate data based on the first secret key.

Through this, the pet owner check the heart rate data and the breathing rate data measured for the pet 10 to more specifically check the health status of the pet 10.

FIG. 2 is a flowchart illustrating an operating method of a measuring apparatus installed in a predetermined detection area indoors, and measuring a health status of a pet according to an exemplary embodiment of the present disclosure.

In step S210, it is monitored whether a sensing signal is generated due to the entry of the pet into the detection area, through the PIR sensor, and it is determined that the pet enters the detection area when it is confirmed that the sensing signal is generated through the PIR sensor, and then a measurement event for measuring the heart rate and the breathing rate of the pet entering the detection area is generated.

In step S220, when the measurement event is generated, the heart rate and the breathing rate of the pet entering the detection area are measured through the radar sensor for a predetermined measurement time to generate heart rate data for a change in heart rate for the measurement time, and generate breathing rate data for the change in breathing rate for the measurement time.

In step S230, it is determined whether there is an abnormality in the health status of the pet entering the detection area based on the heart rate data and the breathing rate data, and when it is determined that there is the abnormality, a notification message for notifying that the health status of a pet is abnormal is transmitted to an electronic terminal of a predetermined pet owner.

In this case, according to an exemplary embodiment of the present disclosure, step S230 may include maintaining a normal data storage storing predetermined normal heart rate data, wherein the normal heart rate data is data for a change in heart rate obtained from a pet in a normal health status for a time which is the same as the measurement time, and predetermined normal breathing rate data, wherein the normal breathing rate data is data for a change in breathing rate obtained from the pet in the normal health status for the time which is the same as the measurement time, sampling, when the heart rate data and the breathing rate data are generated, the heart rate to obtain a plurality of sample heart rates from the heart rate data at a predetermined sampling period interval, and samples the breathing rate from the breathing rate data at the sampling period interval to obtain a plurality of sample breathing rates, sampling the heart rate from the normal heart rate data at the sampling period interval to obtain a plurality of normal sample heart rates, and samples the breathing rate from the normal breathing rate data at the sampling period interval to obtain a plurality of normal sample breathing rates, measuring a first dissimilarity between the plurality of sample heart rates and the plurality of normal sample heat rates, and a second dissimilarity between the plurality of sample breathing rates and the plurality of normal sample breathing rates, and then determines whether the health status of the pet entering the detection area is abnormal based on the first dissimilarity and the second dissimilarity, and transmitting, to the electronic terminal of the pet owner, the notification message for notifying that the health status of the pet is abnormal when it is determined that the health status of the pet entering the detection area is abnormal.

In this case, according to an exemplary embodiment of the present disclosure, the determining may include performing L1 normalization of scaling a size so that the total sum becomes 1 with respect to the plurality of sample heart rates, and then generating a first probability distribution having normalized values as a probability, and performing the L1 normalization of scaling a size so that the total sum becomes 1 with respect to the plurality of normal sample heart rates, and then generating a second probability distribution having normalized values as the probability, and then measuring a Kullback-Leibler Divergence between the first probability distribution and the second probability distribution as the first dissimilarity between the plurality of sample heart rates and the plurality of normal sample heart rates, and performing L1 normalization of scaling a size so that a total sum becomes 1 with respect to the plurality of sample breathing rates, and then generating a third probability distribution having normalized values as a probability, and performing the L1 normalization of scaling the size so that the total sum becomes 1 with respect to the plurality of normal sample breathing rates, and then generating a fourth probability distribution having normalized values as the probability, and then measuring a Kullback-Leibler Divergence between the third probability distribution and the fourth probability distribution as the second dissimilarity between the plurality of sample breathing rates and the plurality of normal sample breathing rates.

Further, according to an exemplary embodiment of the present disclosure, in the determining, when the first dissimilarity and the second dissimilarity are measured, the first dissimilarity may be compared with a predetermined first threshold, and the second dissimilarity may be compared with a predetermined second threshold, and when the first dissimilarity is confirmed to exceed the first threshold, or the second dissimilarity is confirmed to exceed the second threshold, it may be determined that the health status of the pet entering the detection area is abnormal, and when it is confirmed that the first dissimilarity does not exceed the first threshold, and at the same time, it is confirmed that the second dissimilarity does not exceed the second threshold, it may be determined that the health status of the pet entering the detection area is abnormal only when it is confirmed that a value acquired by averaging an error between the first threshold and the first dissimilarity and an error between the second threshold and the second dissimilarity is equal to or less than a predetermined determination reference value.

Further, according to an exemplary embodiment of the present disclosure, an operating method of the measuring apparatus may further include: maintaining a key storage storing a first secret key and a second secret key for data encryption, which are pre-shared with the electronic terminal of the pet owner, wherein different selection probabilities constituted by percentages are assigned to the first secret key and the second secret key, respectively; when receiving a providing request command of the heart rate data and the breathing rate data from the electronic terminal of the pet owner after the notification message is transmitted to the electronic terminal of the pet owner, generating a transmission event for encrypting the heart rate data and the breathing rate data, and transmitting the encrypted heart rate data and breathing rate data to the electronic terminal of the pet owner; checking a number corresponding to a day at a current date and a number corresponding to a minute at a current time, and calculating a product between both numbers, and then performing a modulo operation using 101 as a divisor with respect to a calculated value to generate a result value constituted by integers between 0 and 100; selecting, as a reference probability, a selection probability having a smaller value among the selection probabilities assigned to the first secret key and the second secrete key, and then comparing the result value and the reference probability, and selecting any one secret key having the reference probability as the selection probability among the first secret key and the second secret key as a data encryption key when the result value is equal to or less than the reference probability, and selecting the other one secret key not having the reference probability as the selection probability among the first secret key and the second secret key as the data encryption key when the result value is more than the reference probability; and when selection of the data encryption key is completed, encrypting each of the heart rate data and the breathing rate data based on the data encryption key, and transmitting the encryption data to the electronic terminal of the pet owner.

In this case, when the electronic terminal of the pet owner receives the encrypted heart rate data and the encrypted breathing rate data from the measuring apparatus, the electronic terminal of the pet owner may check the number corresponding to the day at the current date and the number corresponding to the minute at the current time, and calculate a product between both numbers, and then perform a modulo operation using 101 as a divisor with respect to the calculated value to generate the result value which is constituted by integers between 0 and 100, and check the selection probabilities assigned to the first secret key and the second secret key stored in the electronic terminal of the pet owner, and select the selection probability of the smaller value among the selection probabilities assigned to the first secret key and the second secret key as the reference probability, and then compare the result value and the reference probability, and selects any one secret key having the reference probability as the selection probability among the first secret key and the second secret key as a data decryption key when the result value is equal to or less than the reference probability, and select the other one secret key not having the reference probability as the selection probability among the first secret key and the second secret key as the data decryption key, and then decrypt each of the encrypted heart rate data and the encrypted breathing rate data based on the data decryption key, when the result value is more than the reference probability.

Hereinabove, the operating method of the measuring apparatus according to an exemplary embodiment of the present disclosure is described with reference to FIG. 2. Here, since the operating method of the measuring apparatus according to an exemplary embodiment of the present disclosure may correspond to the configuration of the operation of the measuring apparatus 110 described by using FIG. 1, a more detailed description thereof will be omitted.

The operating method of the measuring apparatus according to an exemplary embodiment of the present disclosure may be implemented by a computer program stored in a storage medium for executing the computer program through coupling with a computer.

Further, the operating method of the measuring apparatus according to an exemplary embodiment of the present disclosure may be implemented in a program command type which may be performed through various computer means and recorded in a computer readable medium. The computer readable medium may include a program command, a data file, a data structure, etc., singly or combinationally. The program command recorded in the medium may be specially designed and configured for the present disclosure, or may be publicly known to and used by those skilled in the computer software field. An example of the computer readable recording medium includes magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program command. An example of the program command includes a high-level language code executable by a computer by using an interpreter and the like, as well as a machine language code created by a compiler.

As described above, the present disclosure has been described by specified matters such as detailed components, and the like and limited exemplary embodiments and drawings, but the description is just provided to assist more overall understanding of the present disclosure and the present disclosure is not limited to the exemplary embodiment and various modifications and changes can be made by those skilled in the art from such a disclosure.

Accordingly, the spirit of the present disclosure should not be defined only by the described exemplary embodiments, and it should be appreciated that claims to be described below and all which are equivalent to the claims or equivalently modified are included in the scope of the present disclosure.

What is claimed is:

1. A measuring apparatus installed in a predetermined detection area indoors, and measuring a health status of a pet, comprising:

a passive infrared (PIR) sensor for detecting a pet entering the detection area;

a radar sensor for measuring a heart rate and a breathing rate of the pet entering the detection area;

a measurement event generator monitoring whether a sensing signal is generated due to the entry of the pet into the detection area, through the PIR sensor, and determining that the pet enters the detection area when it is confirmed that the sensing signal is generated through the PIR sensor, and then generating a measurement event for measuring the heart rate and the breathing rate of the pet entering the detection area;

a data generator measuring, when the measurement event is generated, the heart rate and the breathing rate of the pet entering the detection area through the radar sensor for a predetermined measurement time to generate heart rate data for a change in heart rate for the measurement time, and generating breathing rate data for the change in breathing rate for the measurement time; and a notification transmitter determining whether there is an abnormality in the health status of the pet entering the detection area based on the heart rate data and the breathing rate data, and when it is determined that there is the abnormality, transmitting, to an electronic terminal of a predetermined pet owner, a notification message for notifying that the health status of the pet is abnormal, wherein the notification transmitter includes:

a normal data storage storing predetermined normal heart rate data, wherein the normal heart rate data is data for a change in heart rate obtained from a pet in a normal health status for a time which is the same as the measurement time, and predetermined normal breathing rate data, wherein the normal breathing rate data is data for a change in breathing rate obtained from the pet in the normal health status for the time which is the same as the measurement time;

a first sampler sampling, when the heart rate data and the breathing rate data are generated through the data generator, the heart rate to obtain a plurality of sample heart rates from the heart rate data at a predetermined sampling period interval, and sampling the breathing rate from the breathing rate data at the sampling period interval to obtain a plurality of sample breathing rates;

a second sampler sampling the heart rate from the normal heart rate data at the sampling period interval to obtain a plurality of normal sample heart rates, and sampling the breathing rate from the normal breathing rate data at the sampling period interval to obtain a plurality of normal sample breathing rates;

a determinator measuring a first dissimilarity between the plurality of sample heart rates and the plurality of normal sample heart rates, and a second dissimilarity between the plurality of sample breathing rates and the plurality of normal sample breathing rates, and then determining whether the health status of the pet entering the detection area is abnormal based on the first dissimilarity and the second dissimilarity; and a transmission processor transmitting, to the electronic terminal of the pet owner, the notification message for notifying that the health status of the pet is abnormal when it is determined that the health status of the pet entering the detection area is abnormal, wherein the determinator compares, when the first dissimilarity and the second dissimilarity are measured, the first dissimilarity with a predetermined first threshold, and compare the second dissimilarity with a predetermined second threshold, and when the first dissimilarity is confirmed to exceed the first threshold, or the second dissimilarity is confirmed to exceed the second threshold, determines that the health status of the pet entering the detection area is abnormal, and determines, when it is confirmed that the first dissimilarity does not exceed the first threshold, and at the same time, it is confirmed that the second dissimilarity does not exceed the second threshold, that the health status of the pet entering the detection area is abnormal only when it is confirmed that a value acquired by averaging an error between the first threshold and the first dissimilarity and an error between the second threshold and the second dissimilarity is equal to or less than a predetermined determination reference value.

2. The measuring apparatus of claim 1, wherein the determinator includes:

a first dissimilarity measurer performing L1 normalization of scaling a size so that the total sum becomes 1 with respect to the plurality of sample heart rates, and then generating a first probability distribution having normalized values as a probability, and performing the L1 normalization of scaling a size so that the total sum becomes 1 with respect to the plurality of normal sample heart rates, and then generating a second probability distribution having normalized values as the probability, and then measuring a Kullback-Leibler Divergence between the first probability distribution and the second probability distribution as the first dissimilarity between the plurality of sample heart rates and the plurality of normal sample heart rates; and a second dissimilarity measurer performing L1 normalization of scaling a size so that a total sum becomes 1 with respect to the plurality of sample breathing rates, and then generating a third probability distribution having normalized values as a probability, and performing the L1 normalization of scaling the size so that the total sum becomes 1 with respect to the plurality of normal sample breathing rates, and then generating a fourth probability distribution having normalized values as the probability, and then measuring a Kullback-Leibler Divergence between the third probability distribution and the fourth probability distribution as the second dissimilarity between the plurality of sample breathing rates and the plurality of normal sample breathing rates.

3. The measuring apparatus of claim 1, further comprising:

a key storage storing a first secret key and a second secret key for data encryption, which are pre-shared with the electronic terminal of the pet owner, wherein different selection probabilities constituted by percentages are assigned to the first secret key and the second secret key, respectively;

a transmission event generator generating a transmission event for encrypting the heart rate data and the breathing rate data, and transmitting the encrypted heart rate data and breathing rate data to the electronic terminal of the pet owner when receiving a providing request command of the heart rate data and the breathing rate data from the electronic terminal of the pet owner after the notification message is transmitted to the electronic terminal of the pet owner;

a generator checking a number corresponding to a day at a current date and a number corresponding to a minute at a current time, and calculating a product between both numbers, and then performing a modulo operation using 101 as a divisor with respect to a calculated value to generate a result value constituted by integers between 0 and 100;

a key selector selecting, as a reference probability, a selection probability having a smaller value among the selection probabilities assigned to the first secret key and the second secret key, and then comparing the result value and the reference probability, and selecting any one secret key having the reference probability as the selection probability among the first secret key and the second secret key as a data encryption key when the result value is equal to or less than the reference probability, and selecting the other one secret key not having the reference probability as the selection probability among the first secret key and the second secret key as the data encryption key when the result value is more than the reference probability; and when selection of the data encryption key is completed, a data transmitter encrypting each of the heart rate data and the breathing rate data based on the data encryption key, and transmitting the encryption data to the electronic terminal of the pet owner, wherein when the electronic terminal of the pet owner receives the encrypted heart rate data and the encrypted breathing rate data from the measuring apparatus, the electronic terminal of the pet owner checks the number corresponding to the day at the current date and the number corresponding to the minute at the current time, and calculates a product between both numbers, and then performs a modulo operation using 101 as a divisor with respect to the calculated value to generate the result value which is constituted by integers between 0 and 100, and checks the selection probabilities assigned to the first secret key and the second secret key stored in the electronic terminal of the pet owner, and selects the selection probability of the smaller value among the selection probabilities assigned to the first secret key and the second secret key as the reference probability, and then compares the result value and the reference probability, and selects any one secret key having the reference probability as the selection probability among the first secret key and the second secret key as a data decryption key when the result value is equal to or less than the reference probability, and selects the other one secret key not having the reference probability as the selection probability among the first secret key and the second secret key as the data decryption key, and then decrypts each of the encrypted heart rate data and the encrypted breathing rate data based on the data decryption key, when the result value is more than the reference probability.

4. An operating method of a measuring apparatus installed in a predetermined detection area indoors, and measuring a health status of a pet, comprising:

monitoring whether a sensing signal is generated due to the entry of the pet into the detection area, through a passive infrared (PIR) sensor, and determining that the pet enters the detection area when it is confirmed that the sensing signal is generated through the PIR sensor, and then generating a measurement event for measuring the heart rate and the breathing rate of the pet entering the detection area;

measuring, when the measurement event is generated, the heart rate and the breathing rate of the pet entering the detection area through a radar sensor for a predetermined measurement time to generate heart rate data for a change in heart rate for the measurement time, and generating breathing rate data for the change in breathing rate for the measurement time; and determining whether there is an abnormality in the health status of the pet entering the detection area based on the heart rate data and the breathing rate data, and when it is determined that there is the abnormality, transmitting, to an electronic terminal of a predetermined pet owner, a notification message for notifying that the health status of the pet is abnormal, wherein the determining the abnormality includes:

maintaining a normal data storage storing predetermined normal heart rate data, wherein the normal heart rate data is data for a change in heart rate obtained from a pet in a normal health status for a time which is the same as the measurement time, and predetermined normal breathing rate data, wherein the normal breathing rate data is data for a change in breathing rate obtained from the pet in the normal health status for the time which is the same as the measurement time;

sampling, when the heart rate data and the breathing rate data are generated, the heart rate to obtain a plurality of sample heart rates from the heart rate data at a predetermined sampling period interval, and sampling the breathing rate from the breathing rate data at the sampling period interval to obtain a plurality of sample breathing rates;

sampling the heart rate from the normal heart rate data at the sampling period interval to obtain a plurality of normal sample heart rates, and sampling the breathing rate from the normal breathing rate data at the sampling period interval to obtain a plurality of normal sample breathing rates;

measuring a first dissimilarity between the plurality of sample heart rates and the plurality of normal sample heart rates, and a second dissimilarity between the plurality of sample breathing rates and the plurality of normal sample breathing rates, and then determining whether the health status of the pet entering the detection area is abnormal based on the first dissimilarity and the second dissimilarity; and transmitting, to the electronic terminal of the pet owner, the notification message for notifying that the health status of the pet is abnormal when it is determined that the health status of the pet entering the detection area is abnormal, wherein in the determining the health status of the pet, when the first dissimilarity and the second dissimilarity are measured, the first dissimilarity is compared with a predetermined first threshold, and the second dissimilarity is compared with a predetermined second threshold, and when the first dissimilarity is confirmed to exceed the first threshold, or the second dissimilarity is confirmed to exceed the second threshold, it is determined that the health status of the pet entering the detection area is abnormal, and when it is confirmed that the first dissimilarity does not exceed the first threshold, and at the same time, it is confirmed that the second dissimilarity does not exceed the second threshold, it is determined that the health status of the pet entering the detection area is abnormal only when it is confirmed that a value acquired by averaging an error between the first threshold and the first dissimilarity and an error between the second threshold and the second dissimilarity is equal to or less than a predetermined determination reference value.

5. The operating method of a measuring apparatus of claim 4, wherein the measuring the first dissimilarity and the second dissimilarity includes:

performing L1 normalization of scaling a size so that the total sum becomes 1 with respect to the plurality of sample heart rates, and then generating a first probability distribution having normalized values as a probability, and performing the L1 normalization of scaling a size so that the total sum becomes 1 with respect to the plurality of normal sample heart rates, and then generating a second probability distribution having normalized values as the probability, and then measuring a Kullback-Leibler Divergence between the first probability distribution and the second probability distribution as the first dissimilarity between the plurality of sample heart rates and the plurality of normal sample heart rates; and performing L1 normalization of scaling a size so that a total sum becomes 1 with respect to the plurality of sample breathing rates, and then generating a third probability distribution having normalized values as a probability, and performing the L1 normalization of scaling the size so that the total sum becomes 1 with respect to the plurality of normal sample breathing rates, and then generating a fourth probability distribution having normalized values as the probability, and then measuring a Kullback-Leibler Divergence between the third probability distribution and the fourth probability distribution as the second dissimilarity between the plurality of sample breathing rates and the plurality of normal sample breathing rates.

6. The operating method of a measuring apparatus of claim 4, further comprising:

maintaining a key storage storing a first secret key and a second secret key for data encryption, which are pre-shared with the electronic terminal of the pet owner, wherein different selection probabilities constituted by percentages are assigned to the first secret key and the second secret key, respectively;

when receiving a providing request command of the heart rate data and the breathing rate data from the electronic terminal of the pet owner after the notification message is transmitted to the electronic terminal of the pet owner, generating a transmission event for encrypting the heart rate data and the breathing rate data, and transmitting the encrypted heart rate data and breathing rate data to the electronic terminal of the pet owner;

checking a number corresponding to a day at a current date and a number corresponding to a minute at a current time, and calculating a product between both numbers, and then performing a modulo operation using 101 as a divisor with respect to a calculated value to generate a result value constituted by integers between 0 and 100;

selecting, as a reference probability, a selection probability having a smaller value among the selection probabilities assigned to the first secret key and the second secret key, and then comparing the result value and the reference probability, and selecting any one secret key having the reference probability as the selection probability among the first secret key and the second secret key as a data encryption key when the result value is equal to or less than the reference probability, and selecting the other one secret key not having the reference probability as the selection probability among the first secret key and the second secret key as the data encryption key when the result value is more than the reference probability; and when selection of the data encryption key is completed, encrypting each of the heart rate data and the breathing rate data based on the data encryption key, and transmitting the encryption data to the electronic terminal of the pet owner, wherein when the electronic terminal of the pet owner receives the encrypted heart rate data and the encrypted breathing rate data from the measuring apparatus, the electronic terminal of the pet owner checks the number corresponding to the day at the current date and the number corresponding to the minute at the current time, and calculates a product between both numbers, and then performs a modulo operation using 101 as a divisor with respect to the calculated value to generate the result value which is constituted by integers between 0 and 100, and checks the selection probabilities assigned to the first secret key and the second secret key stored in the electronic terminal of the pet owner, and selects the selection probability of the smaller value among the selection probabilities assigned to the first secret key and the second secret key as the reference probability, and then compares the result value and the reference probability, and selects any one secret key having the reference probability as the selection probability among the first secret key and the second secret key as a data decryption key when the result value is equal to or less than the reference probability, and selects the other one secret key not having the reference probability as the selection probability among the first secret key and the second secret key as the data decryption key, and then decrypts each of the encrypted heart rate data and the encrypted breathing rate data based on the data decryption key, when the result value is more than the reference probability.

7. A non-transitory computer readable recording medium having a program recorded therein for allowing a computer to execute an operating method of a measuring apparatus installed in a predetermined detection area indoors, and measuring a health status of a pet, comprising:

monitoring whether a sensing signal is generated due to the entry of the pet into the detection area, through a passive infrared (PIR) sensor, and determining that the pet enters the detection area when it is confirmed that the sensing signal is generated through the PIR sensor, and then generating a measurement event for measuring the heart rate and the breathing rate of the pet entering the detection area;

measuring, when the measurement event is generated, the heart rate and the breathing rate of the pet entering the detection area through a radar sensor for a predetermined measurement time to generate heart rate data for a change in heart rate for the measurement time, and generating breathing rate data for the change in breathing rate for the measurement time; and determining whether there is an abnormality in the health status of the pet entering the detection area based on the heart rate data and the breathing rate data, and when it is determined that there is the abnormality, transmitting, to an electronic terminal of a predetermined pet owner, a notification message for notifying that the health status of the pet is abnormal, wherein the determining the abnormality includes:

maintaining a normal data storage storing predetermined normal heart rate data, wherein the normal heart rate data is data for a change in heart rate obtained from a pet in a normal health status for a time which is the same as the measurement time, and predetermined normal breathing rate data, wherein the normal breathing rate data is data for a change in breathing rate obtained from the pet in the normal health status for the time which is the same as the measurement time;

sampling, when the heart rate data and the breathing rate data are generated, the heart rate to obtain a plurality of sample heart rates from the heart rate data at a predetermined sampling period interval, and sampling the breathing rate from the breathing rate data at the sampling period interval to obtain a plurality of sample breathing rates;

sampling the heart rate from the normal heart rate data at the sampling period interval to obtain a plurality of normal sample heart rates, and sampling the breathing rate from the normal breathing rate data at the sampling period interval to obtain a plurality of normal sample breathing rates;

measuring a first dissimilarity between the plurality of sample heart rates and the plurality of normal sample heart rates, and a second dissimilarity between the plurality of sample breathing rates and the plurality of normal sample breathing rates, and then determining whether the health status of the pet entering the detection area is abnormal based on the first dissimilarity and the second dissimilarity; and transmitting, to the electronic terminal of the pet owner, the notification message for notifying that the health status of the pet is abnormal when it is determined that the health status of the pet entering the detection area is abnormal, wherein in the determining the health status of the pet, when the first dissimilarity and the second dissimilarity are measured, the first dissimilarity is compared with a predetermined first threshold, and the second dissimilarity is compared with a predetermined second threshold, and when the first dissimilarity is confirmed to exceed the first threshold, or the second dissimilarity is confirmed to exceed the second threshold, it is determined that the health status of the pet entering the detection area is abnormal, and when it is confirmed that the first dissimilarity does not exceed the first threshold, and at the same time, it is confirmed that the second dissimilarity does not exceed the second threshold, it is determined that the health status of the pet entering the detection area is abnormal only when it is confirmed that a value acquired by averaging an error between the first threshold and the first dissimilarity and an error between the second threshold and the second dissimilarity is equal to or less than a predetermined determination reference value.

* * * * *